United States Patent
Kovesdi et al.

(10) Patent No.: US 9,561,291 B2
(45) Date of Patent: Feb. 7, 2017

(54) METHODS OF TARGETING T-CELLS TO TUMORS

(71) Applicants: Imre Kovesdi, Rockville, MD (US); Tibor Bakács, Budapest (HU); Miklós Szabó, Göd (HU)

(72) Inventors: Imre Kovesdi, Rockville, MD (US); Tibor Bakács, Budapest (HU); Miklós Szabó, Göd (HU)

( * ) Notice: Subject to any disclaimer, the term of this patent is extended or adjusted under 35 U.S.C. 154(b) by 30 days.

(21) Appl. No.: 13/838,667

(22) Filed: Mar. 15, 2013

(65) Prior Publication Data
US 2014/0271687 A1 Sep. 18, 2014

(51) Int. Cl.
A61K 47/48 (2006.01)

(52) U.S. Cl.
CPC ..... *A61K 47/48746* (2013.01); *A61K 47/4863* (2013.01); *A61K 47/48615* (2013.01); *A61K 47/48638* (2013.01); *A61K 47/48753* (2013.01)

(58) Field of Classification Search
CPC ............... A61K 47/48746; A61K 47/48615; A61K 47/48753; A61K 47/4863; A61K 47/4813
See application file for complete search history.

(56) References Cited

U.S. PATENT DOCUMENTS

| | | | | |
|---|---|---|---|---|
| 5,525,338 | A * | 6/1996 | Goldenberg | 424/178.1 |
| 6,075,010 | A * | 6/2000 | Theodore et al. | 514/23 |
| 6,077,499 | A * | 6/2000 | Griffiths et al. | 424/1.49 |
| 7,229,628 | B1 | 6/2007 | Allison et al. | |
| 2008/0152655 | A1* | 6/2008 | Liu et al. | 424/158.1 |
| 2010/0189642 | A1* | 7/2010 | Morgenstern | A61K 51/1045 424/1.49 |
| 2010/0272723 | A1* | 10/2010 | Bernett et al. | 424/139.1 |

FOREIGN PATENT DOCUMENTS

WO WO9954440 * 10/1999
WO 01/97855 A2 12/2001

OTHER PUBLICATIONS

Jubala et al., Vet Pathol 42: 468-476, 2005.*
Yu et al., Investigative Ophthalmology & Visual Science 49(2): 522-527, Feb. 2008.*
Stancovski et al., PNAS, 88: 8691-8695, 1991.*
Golay et al., Archives of Biochemistry and Biophysics 526: 146-153, 2012.*
Colman et al., Research in Immunology (145(1):33-36, 1994.*
Bakacs, T. et al., A bispecific antibody prolongs survival in mice bearing lung metastases of syngeneic mammary adenocarcinoma. Int.Immunol., 7(6): 947-955 (1995).
Bakacs, T. et al., Interesting possibilities to improve the safety and efficacy of ipilimumab (Yervoy). Pharmacol.Res., 66(2): 192-197 (2012).
Beckman, R. A. et al., Antibody constructs in cancer therapy: protein engineering strategies to improve exposure in solid tumors. Cancer, 109(2): 170-179 (2007).
Curran, M. A. et al., Response to "Ipilimumab (Yervoy) and the TGN1412 catastrophe". Immunobiology 217: 590-592 (2012).
Farzaneh, L. et al., The strange case of TGN1412. Cancer Immunol Immunother., 56(2): 129-134 (2007).
Frampas, E. et al., Pretargeted radioimmunotherapy of colorectal cancer metastases: models and pharmacokinetics predict influence of the physical and radiochemical properties of the radionuclide. Eur.J Nucl.Med Mol.Imaging, 38 (12): 2153-2164 (2011).
Phillips, K. E. et al., IL-2Ralpha-Directed monoclonal antibodies provide effective therapy in a murine model of adult T-cell leukemia by a mechanism other than blockade of IL-2/IL-2Ralpha interaction. Cancer Res., 60(24): 6977-6984 (2000).
Porter, D. L. et al., Chimeric Antigen Receptor-Modified T Cells in Chronic Lymphoid Leukemia. N Engl.J.Med., (2011).
Renner, C. et al., Cure of Xenografted Human Tumors by Bispecific Monoclonal Antibodies and Human T Cells. Science, 264(5160): 833-835 (1994).
Robert, C. et al., Ipilimumab plus Dacarbazine for Previously Untreated Metastatic Melanoma. N Engl J Med, 364 (26): 2517-2526 (2011).
Rosenberg, S. A. et al., Adoptive cell transfer: a clinical path to effective cancer immunotherapy. Nat.Rev.Cancer, 8(4): 299-308 (2008).
Scott, A. M. et al., Antibody therapy of cancer. Nat Rev Cancer, 12(4): 278-287 (2012).
Sharkey, R. M. et al., Cancer radioimmunotherapy. Immunotherapy., 3(3): 349-370 (2011).
Stein, R. et al., Characterization of a New Humanized Anti-CD20 Monoclonal Antibody, Immu-106, and Its Use in Combination with the Humanized Anti-CD22 Antibody, Epratuzumab, for the Therapy of Non-Hodgkin's Lymphoma. Clin Cancer Res., 10(8): 2868-2878 (2004).
Szabados, T. et al., Sufficient to recognize self to attack non-self: Blueprint for a one-signal T cell model. Journal of Biological Systems, 19(2): 299-317 (2011).
Grupp, S. A. et al., Chimeric Antigen Receptor-Modified T Cells for Acute Lymphoid Leukemia. N. Engl. J. Med.; 368: 1509-1518 (2013).
Zimmerman et al.: "Unleashing the clinical power of T cells: CD19/CD3 bi-specific T cell engager (BiTE®) antibody construct blinatumomab as a potential therapy", International Immunology, 2014, vol. 27, No. 1, pp. 31-37.

* cited by examiner

Primary Examiner — Phuong Huynh
(74) Attorney, Agent, or Firm — Jason D. Voight

(57) ABSTRACT

The invention provides a method of targeting T-cells to tumor cells using a tumor-associated antigen (TAA) specific antibody and a T-cell specific antibody, wherein the two antibodies can bind to each other through a high affinity avidin/biotin or streptavidin/biotin connection. The invention further provides methods to target activated T-cells to different tumor types by using a T-cell specific antibody that is specific to an activated T-cell surface molecule like CTLA-4.

13 Claims, 5 Drawing Sheets

METHODS OF TARGETING T-CELLS TO TUMORS

FIELD OF THE INVENTION

This invention pertains to novel immunological methods related to selective targeting of T-cells to cancer cells with antibodies, and methods of administering such antibodies.

BACKGROUND OF THE INVENTION

Within the next decade, cancer is likely to replace heart disease as the leading cause of U.S. deaths, according to forecasts by the NCI and the Centers for Disease Control and Prevention. Apparently, new ideas are desperately needed for tumor cells destruction.

One possible solution is to deliver tumor specific T-cells to patients. Porter et al. (Porter et al., N. Engl. J. Med., (2011)) have solved the problem of retargeting and co-stimulation by demonstrating that efficient retargeting of T-cells can be achieved by a genetically engineered chimeric "bipartite" antigen receptor. Such a bipartite receptor consists of two signaling modules, (i) an antibody conferring new antigen specificity for the B-cell antigen CD19 and (ii) a co-stimulatory domain that expanded tumor-reactive T-cells, which retained their functional phenotype, including in vivo cytolytic activity and the ability to travel to tumor sites without prematurely succumbing to apoptosis. A low dose ($\sim 1.5\times10^5$ cells/kgbw) of autologous chimeric antigen receptor-modified T-cells reinfused into a patient with refractory chronic lymphocytic leukemia (CLL) expanded to a level that was more than 1000 times as high as the initial engraftment level in vivo and was able to eliminate about $10^{12}$ tumor cells in a CLL patient.

Unlike with other therapeutic approaches, chimeric antigen receptor modified T cells have the potential to replicate in vivo. The long-term persistence of such chimeric T cells could lead to sustained tumor control and obviate the need for repeated infusions of antibodies.

A major problem with adoptive T-cell therapy is, however, that essentially a new reagent needs to be created for each patient. Such a labor-intensive therapy does not easily fit into current modes of commercial practice of pharmaceutical and biotechnology companies (Rosenberg et al., Nat. Rev. Cancer, 8, 299-308 (2008)).

Monoclonal antibodies (mAbs) are emerging as one of the major class of therapeutic agents in the treatment of many human diseases, particularly in cancer and immunological disorders. As of 2010, 28 mAbs have been approved by the United States Food and Drug Administration for clinical applications. Therapeutic mAbs target tumor associated antigens (TAA) expressed by tumor cells (Scott et al., Nat Rev Cancer, 12, 278-287 (2012)).

Tumor cell killing by therapeutic antibodies is mediated by several mechanisms such as direct tumor cell killing (e.g. delivery of a cytotoxic payload by chemotherapy drug, catalytic toxin, radioisotope, or enzyme), immune-mediated tumor cell killing (e.g. via opsonization triggering cytotoxic cells) or vascular and stromal cell ablation (e.g. by modification of biological processes such as growth and apoptosis) as it is demonstrated on FIG. 1 and described in (Scott et al., Nat Rev Cancer, 12, 278-287 (2012)).

Conjugated antibodies are a form of biological guided missiles that combine a targeting moiety with a potent effector molecule that can deliver a payload such as a drug, toxin, small interfering RNA or radioisotope to a tumor cell. Conjugating cytotoxic agents to mAbs has enhanced targeted therapeutic delivery to tumors. Antibody-drug conjugates are now one of the most successful and important new treatment options for lymphomas and solid tumors.

Monoclonal antibodies (mAb) and their fragments, labeled with therapeutic radionuclides, have been used for many years in the development of anticancer strategies, with the aim of concentrating radioactivity at the tumor site and sparing normal tissues. When delivered at a sufficient dose and dose rate to a neoplastic mass, radiation can kill tumor cells. Because cancer frequently presents as a disseminated disease, it is imperative to deliver cytotoxic radiation not only to the primary tumor but also to distant metastases, while reducing exposure of healthy organs as much as possible.

Over 85% of human cancers are solid tumors, which makes them hard to target by antibodies. The largest percentage of the dose of mAb is in the plasma because whole-body distribution predominantly targets organs that are highly perfused with blood. Therefore, mAbs directed against tumor-specific antigens largely remain in the blood; no more than 20% of the administered dose typically associates with the tumor. In addition, anatomical and physiological properties of solid tumors make them particularly hard to penetrate. Generally only on the order of 0.01% of the injected mAb dose penetrates the tumor (Beckman et al., Cancer, 109, 170-179 (2007)).

Molecular genetics and chemical modifications to mAbs have, however, advanced their clinical utility by improving their pharmacokinetic profiles. Penetration is improved by structural modifications. Ab constructs include Fab and Fab'$_2$ fragments, scFvs, multivalent scFvs (e.g., diabodies and tribodies), minibodies (e.g., scFv-CH3 dimers), bispecific Abs, and camel variable functional heavy chain domains. A suitable balance must be found between Ab properties that promote tumor penetration and those that promote tumor retention. Low-affinity Abs penetrate more deeply into the tumor than high-affinity Abs. Due to their smaller size scFv fragments diffuse approximately 6 times faster than IgG (Beckman et al., Cancer, 109, 170-179 (2007)).

The methods of pretargeting involves separating the targeting antibody from the subsequent delivery of an imaging or therapeutic agent that binds to the tumor-localized antibody. This provides enhanced tumor/background ratios and the delivery of a higher therapeutic dose than when antibodies are directly conjugated with radionuclides, as currently practiced in cancer radioimmunotherapy. There are promising clinical results using streptavidin-antibody constructs with biotin-radionuclide conjugates and bispecific antibodies (bsAbs) with hapten-radionuclides in therapy of tumors, (described in, e.g., International Patent Application WO 01/97855, U.S. Pat. No. 7,229,628, and the references cited therein).

Via their Fc-receptors antibodies are also capable to induce immune-mediated tumor cell killing by the induction of phagocytosis, complement activation, or antibody-dependent-cellular cytotoxicity (ADCC).

T-cells are the strongest force of the immune system capable of rejecting entire organ grafts (e.g. kidneys, livers, etc.). In addition, healthy humans carry approximately 3-times more T-cells than NK-cells in their circulation such that their numbers may be sufficient to eliminate most cancer cells after recruitment.

T-cells, however, do not carry activating Fc-receptors, therefore cannot be recruited for the direct elimination of a tumor cell by antibody-mediated cellular cytotoxicity. This shortcoming can be overcome by creating bispecific antibodies (bsAbs) capable of simultaneous binding to two different targets. The idea of using T-cells to efficiently kill tumor cells using bsAbs emerged in the 1980. BsAbs directed against a tumor marker and CD3 have the potential to redirect and activate any circulating T-cells against tumors.

Various bispecific antibody formats such as recombinant tandem bispecific scFvs, bispecific diabodies and tandem bispecific diabodies have been developed. These constructs can specifically bind both the tumor cell and a trigger molecule on a T-cell (e.g. CD2, CD3, CD5, TCRα, TCRβ, TCRγδ and CD28). The best-studied trigger is CD3. The most prominent member of the novel class of recombinant bispecific T-cell engagers (BiTEs) is the CD19- and CD3-directed agent blinatumomab (MT103), which is studied in five ongoing clinical trials.

BsAbs directed against the CD3 of T-cells have a major drawback. Without the secondary signal provided by the interaction between CD28 and one of its ligands (e.g., B7), T-cells are not fully activated, and might even become anergic. The first anti-CD3 bsAbs were thus administered in combination with anti-CD28 antibodies, but the combination yielded mixed results.

The B7-CD28/CTLA-4 co-stimulatory pathway of T-cells plays a pivotal role in maintaining health. Microbes and cytokines produced during innate immune responses induce expression of co-stimulators, such as B7 (CD80/86) molecules, on the antigen presenting cells (APCs). The B7 co-stimulators are recognized by the CD28 receptors of naïve T-cells, providing "signal 2" and in conjunction with antigen recognition ("signal 1") initiate T-cell responses.

Lack of co-stimulation, and the concomitant inadequacy of IL-2 production, prevent subsequent proliferation of the T-cell and induce a state of non-reactivity termed "anergy". This is associated with a block in IL-2 gene transcription and a lack of responsiveness of the affected T-cells to IL-4. Anergy may be overcome with prolonged IL-2 stimulation.

CTLA-4 is a T-cell surface molecule that was originally identified by differential screening of a murine cytolytic T-cell cDNA library. The CTLA-4 is a second receptor for B7. It is a CD28 homologue and is expressed only on activated T-cells. It binds with high affinity to the CD28 ligands, B7-1 (CD80) and B7-2 (CD86).

It is suggested that CTLA-4 can function as a negative regulator of T-cell activation. CTLA-4 receptors of T-cells work as a braking mechanism on T-cell activation that is indispensable to ensure tolerance to self-tissues. If CTLA-4 does not function due to a genetic deficiency or it is blocked by various manipulations, CD28 functions unopposed and swings the balance in favor of immune stimulation resulting in breakdown of tolerance.

Thus, the B7-CD28/CTLA-4 co-stimulatory pathway of T-cells plays a pivotal role in maintaining health. Not surprisingly, both the accelerator (CD28) and the brake operator (CTLA-4) on the immune system were apparently targeted by new therapeutic initiatives in autoimmune disorders and cancer, respectively (Bakacs et al., Pharmacol. Res., 66, 192-197 (2012)). Immunomodulatory antibodies directly targeting receptors involved in checkpoint regulation of immune cells have, however, achieved controversial clinical results.

TGN1412, a monospecific 'superagonistic' CD28 antibody induced systemic T cell activation and severe cytokine release syndrome when injected into six healthy volunteers, and since then concerns have been raised about the use of immunomodulatory molecules.

Anti-CTLA-4 antibodies on the other hand block the T-cell inhibitory receptor CTLA-4. Methods and compositions were provided for increasing the activation of T-cells through a blockade of CTLA-4 signaling. For example, U.S. Pat. No. 7,229,628 discloses binding molecules that specifically interact with the CTLA-4 antigen, but do not activate signaling (blocking agents), were combined with T-cells, in vitro or in vivo. When CTLA-4 signaling is thus blocked, the T-cell response to antigen is released from inhibitory state. As demonstrated in FIG. 2a, B7 ligation of CTLA-4 triggers apoptosis or anergy in T-cell populations. Inhibition of CTLA-4 signaling also prevents apoptosis or anergy in the activated T-cell population as demonstrated in FIG. 2b. Therefore, an anti-CTLA-4 antibody in the presence of tumor specific antigens could provide a superior anti-cancer drug. Unfortunately, the simple delivery of an anti-CTLA-4 mAb like ipilimumab is fraught with problems.

The safety data from 14 completed phase I-III clinical trials of anti-CTLA-4 antibody in 1498 patients with advanced melanoma indicated that immune related adverse events (irAEs) occurred in 64.2% of the patients. The previously proposed mechanism of action of anti-CTLA-4 antibody (i.e., tolerance breakdown) is consistent with the large numbers of irAEs and cannot be reconciled with the basic assumption that in an otherwise healthy individual suffering from cancer, most CTLA-4 expressing T-cells are either effector cells engaged in an anti-tumor response or regulatory T-cells actively opposing that response (Curran et al., Immunobiology, (2012)). This assumption comes from the conventional "two-signal" T cell activation model, which claim that until a foreign antigen (e.g. virus, tumor cell) is present in the body the immune system is at rest, as it is described in (Szabados et al., Journal of Biological Systems, 19, 299-317 (2011)). This model cannot explain the high rate of irAEs in the clinical trials.

There remains a need for novel methods to target activated T-cells to specific cancer cells efficiently and without serious side effects, whose commercialization is feasible. The availability of an off-the-shelf therapy composed of non-cross-resistant killer T cells has the potential to improve the outcome of patients not only with B cell malignancies as described in (Porter et al., N. Engl. J. Med., (2011)) but many others applications which carry a TAA. The present invention provides such a method related to tumor specific and T-cell specific antibodies, as well as their delivery and high affinity binding to each other in vivo. These and other advantages of the invention, as well as additional inventive features, will be apparent from the description of the invention provided herein.

Our invention provides a new, commercially feasible antibody-based method for T cell targeting relying on an alternative explanation for the high rate of irAEs in the anti-CTLA-4 antibody clinical trials.

Such alternative explanation is provided by the "one-signal" T cell model, which assumes that in order to discriminate self and non-self, T lymphocytes need to recognize the much smaller set of self-antigens, rather than the practically unlimited non-self antigen universe. Positively selected T cells form a homeostatic coupled system via internal dialogue with tissue cells through continuous, low affinity complementary TCR-MHC interactions such that a dynamic steady state is achieved. Therefore, a significant (though constantly changing) fraction of T-cells is never at rest, which explains the high rate of irAEs in the above described ipilimumab clinical trials. The existence of such self-reacting activated T cells was predicted by the "one-signal" model several years ago. However, their presence was proved only by the dose-dependent escalation of irAES during the anti-CTLA-4 antibody clinical trials.

The reason for this that the CTLA-4 receptor is a common molecular target that is expressed on both the targeted as well as on the non-targeted T-cells. Since the blockade occurs dose-dependently on all activated CTLA-4 positive T-cells, clearly, the receptor blockade cannot be restricted to the targeted tumor (e.g. melanoma)-specific T-cell population. With an increasing dose of antibody, the kinetics of the interaction is pushed in favor of widespread uncontrolled T-cell expansion causing serious side effects (Farzaneh et al., Cancer Immunol Immunother., 56, 129-134 (2007)). Mechanistically, the immune-related adverse events associated with CTLA-4 blockade represent a transient breakthroughs of otherwise contained pre-existing self-reactive T-cells.

SUMMARY OF THE INVENTION

Accordingly, the invention provides a method of targeting T-cells to tumor cells using a tumor-associated antigen (TAA) specific antibody and a T-cell specific antibody, wherein the two antibodies form a high affinity linkage to each other through an Avidin (Av)/biotin or streptavidin (StAv)/biotin connection after they are consecutively delivered to a mammal. The invention further provides methods to target activated T-cells to different tumor types by using a T-cell specific antibody that is specific to an activated T-cell surface molecule like CTLA-4.

The invention further provides that through the delivery of a first antibody the T-cell targeting will be specific to a TAA and will direct the T-cell antibody complex to the target tumor. The first antibody is chosen according to the tumor being targeted. There are large numbers of TAAs known in the prior art which can be targeted. Examples of TAAs are CEA, Immature laminin receptor, TAG-72, BING-4, BING-4, Calcium-activated chloride channel 2, Cyclin-B1, 9D7, Ep-CAM, EphA3, Telomerase, Mesothelin, SAP-1, Survivin, BAGE, CAGE, GAGE, MAGE, SAGE, XAGE, NY-ESO-1/LAGE-1, PRAME, SSX-2, Melan-A/MART-1, Gp100/pmel17, Tyrosinase, TRP-1/-2, P. polypeptide, MC1R, PSA, β-catenin, BRCA1/2, CDK4, CML66, Fibronectin, MART-2, p53, Ras, TGF-βRII, MUC1, CD19, CD 20.

The invention further provides that the second antibody is specific to a T-cell receptor or co-stimulatory or inhibitory surface molecule. The T-cell surface molecule is chosen according to the types of T-cell being targeted to the tumor. Examples of T-cell surface molecules are CD2, CD3, CD4, CD5, CD6, CD7, CD8, CD25, CD28, CD56, CD137, CD152. Preferably, the T-cell surface molecule is induced on activated T-cells. More preferably the second antibody is specific to the CD137 T-cell receptor, but most preferably the second antibody is specific to the CTLA-4 activated surface molecule. The invention further provides methods for improving the safety and efficacy of the activation of T-cells through an anti-CTLA-4 antibody blockade of CTLA-4 signaling. An important premise of the invention is that administration of anti-CTLA mAb will stimulate all activated T-cells, causing irAEs. The present invention advantageously and unexpectedly avoids such irAEs (Bakacs et al., Pharmacol. Res., 66, 192-197 (2012)).

DETAILED DESCRIPTION OF THE INVENTION

The present invention provides a method of treating a tumor or cancer in a host comprising administering an anti-cancer or anti-tumor effective amount of antibodies of the present invention to a mammalian host in need thereof. The present invention also provides methods of tumor targeting using activated T-cells that has several advantages compared to previous approaches used in the prior art and overcomes some of their major drawbacks.

Activated T-cells are one of the most powerful agents in the mammalian body. T-cells are capable of destroying not only virally infected cells (e.g. as in hepatitis) but also tumor cells provided the latter are connected to T cells via a suitable trigger molecule, which induce cytotoxicity.

T-cells and tumor cells can be brought into contact via antibodies, which are easy to produce and administer, and their therapeutically effective concentrations can be calculated. Therefore, antibodies can be exploited for pretargeting activated T-cells of any specificity and induce killing of targeted cells.

Prior art claims that an anti-CTLA mAb specifically stimulates melanoma (tumor) specific T-cells and regulatory T-cells because in a tumor patient only tumor specific T-cells are activated (Curran et al., Immunobiology, (2012)).

The present invention is based on the assertion that the above claim is incorrect and in a tumor patient not only tumor specific but also self-reactive T-cells are activated. Self-peptides not only select but also sustain the T-cell repertoire continuously providing fundamental activation signals for T-cell survival. Therefore, administration of anti-CTLA mAb will stimulate all activated T-cells including self-reactive T-cells expressing CTLA-4 receptors and will result in a polyclonal T-cells activation. These activated T-cells will attack cancer cells, but will also induce unwanted side effects including severe irAEs.

The present invention provides a method of targeting T-cells to tumor cells using a TAA specific antibody and a T-cell specific antibody, wherein the two antibodies can bind to each other through a high affinity avidin/biotin or streptavidin/biotin connection. The invention further provides methods to target activated T-cells to different tumor types by using a T-cell specific antibody that is specific to an activated T-cell surface molecule. This strategy will avoid unwanted side effects including severe irAEs, which is the major drawback of prior art.

Figure 1:
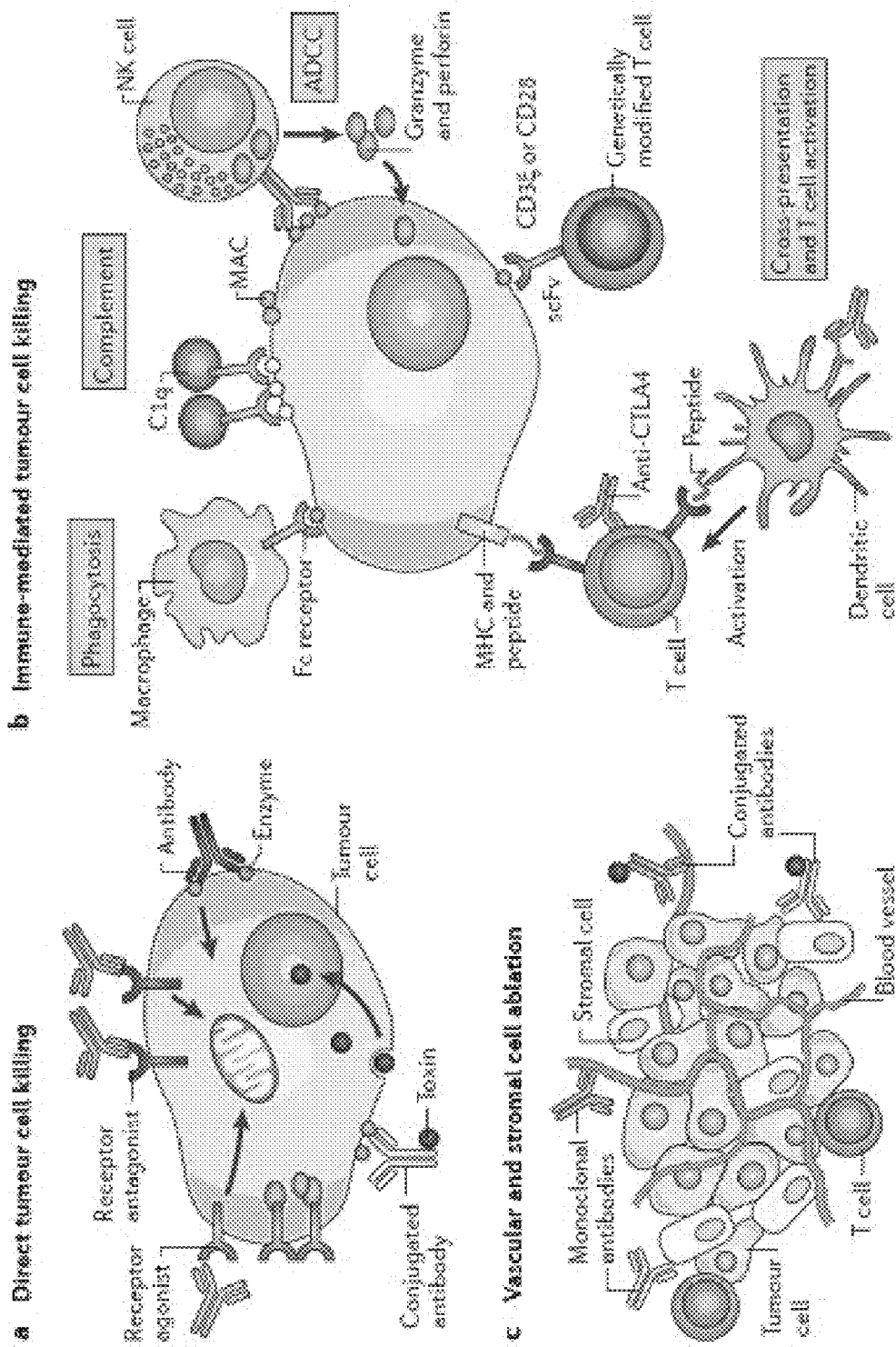
FIG. 1 depicts mechanisms of tumor cell killing by antibodies. (a) Direct tumor cell killing (e.g. delivery of a cytotoxic payload by chemotherapy drug, catalytic toxin, radioisotope, or enzyme), (b) immune-mediated tumor cell killing (e.g. via opsonization triggering cytotoxic cells through dendritic-, T-, NK or macrophages), (c) vascular and stromal cell ablation (e.g. by modification of biological processes such as growth and apoptosis).
Figure 2:
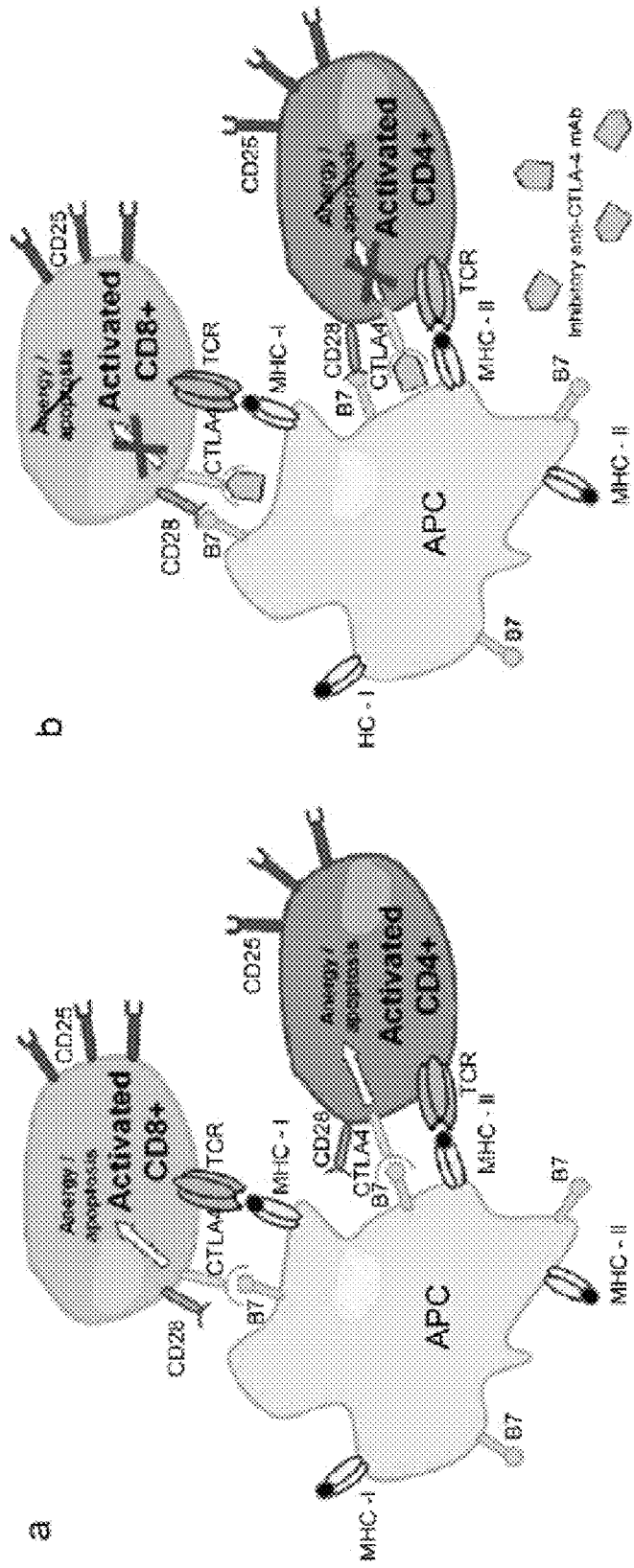
FIG. 2 demonstrates the anti-tumor effects of CTLA-4 blockade. Abbreviations: Ag, antigen; APC, antigen-presenting cell; CTLA-4, cytotoxic T lymphocyte-associated antigen 4; MHC, major histocompatibility complex; TCR T-cell receptor; Treg, regulatory T-cell.
Figure 3:
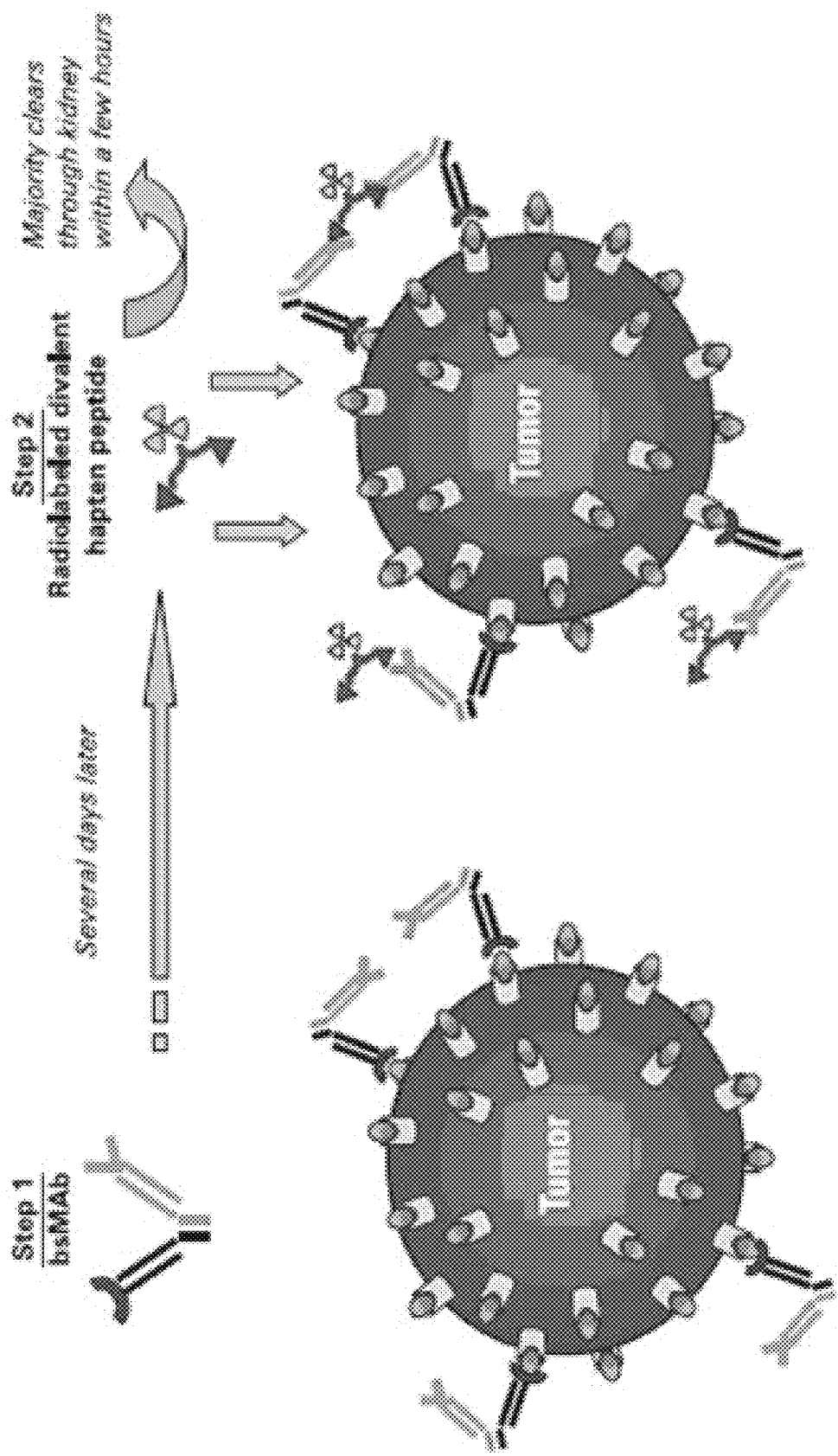
FIG. 3 illustrates the use of tumor cell pretargeting with bsAbs and radionucleotides.
Figure 5:
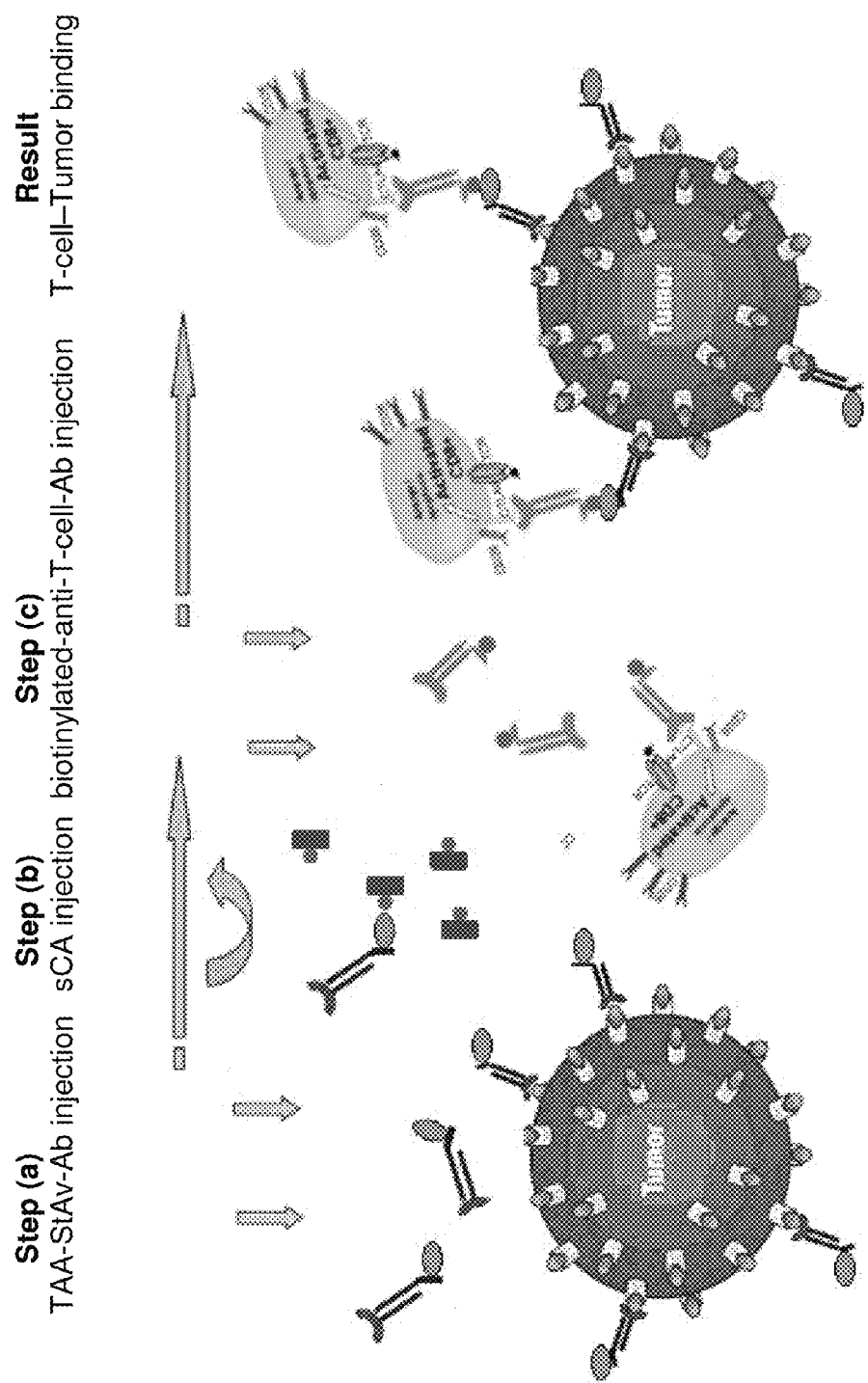
FIG. 5 illustrates the use of tumor cell pretargeting with a TAA specific streptavidin conjugated mAb (mAb-StAv) followed by the delivery of a clearing agent and then delivery of a biotinylated T-cell specific mAb resulting in T-cell targeting of the tumor.

Present invention claims that the above strategy can be successful by building on a pretargeting approach that has been developed for radioimmunodetection and radioimmunotherapy (Sharkey et al., Immunotherapy., 3, 349-370 (2011)), as demonstrated in FIG. 3, but have not been proposed for T-cell pretargeting use as demonstrated in FIG. 5. Pretargeting a tumor via an anti-tumor antibody conjugated with streptavidin would tether activated T-cells on the surface of tumor cells via a subsequently delivered biotin modified anti-CTLA-4 antibody for effective therapy.

The most preferred embodiment of the present invention provides methods for improving the safety and efficacy of the activation of T-cells through an anti-CTLA-4 antibody blockade of CTLA-4 signaling that would dampen irAEs in a mammalian host. The method is comprised of: (a) administering first a StAv conjugated tumor specific antibody to a mammalian host in an amount sufficient to bind to tumor cells; (b) administering a biotinylated clearing compound and allowing sufficient amount of time for the non-tumor bound first antibody to be eliminated from the mammalian host; (c) administering a second biotinylated CTLA-4 receptor specific antibody to the mammalian host that binds activated T-cells and then via the CTLA-4 antibody binds to the first tumor specific antibody present on the tumor cell surface resulting in tumor destruction as it is demonstrated on FIG. 5.

From a practical perspective the biotinylated CTLA-4 antibody and the clearing compound are general reagents that would be applicable to all cancer types, while the StAv conjugated tumor specific antibody will be administered according to the specific needs of the patient depending of the type of cancer or tumor.

First, a streptavidin (StAv) conjugated anti-tumor antibody (e.g. anti-CD19 or anti-CD20 mAb of chronic lymphocytic leukemia (CLL)) is administered, which is followed by the delivery of biotin-labeled a T-cell co-stimulatory antibody (e.g. anti-CTLA-4 mAb). Co-stimulatory antibodies endow cells with the ability to travel to tumor sites without prematurely succumbing to apoptosis. Then, streptavidin's ultra-high affinity for biotin ($K_D$, $10^{-15}$ M) ensures that all T-cells carrying biotin-labeled co-stimulatory antibodies will be captured on the surface of tumor cells. This way, the forces of the immune system liberated by the co-stimulatory antibody could be tethered to the tumor cells without collateral damage to normal cells.

Figure 4:
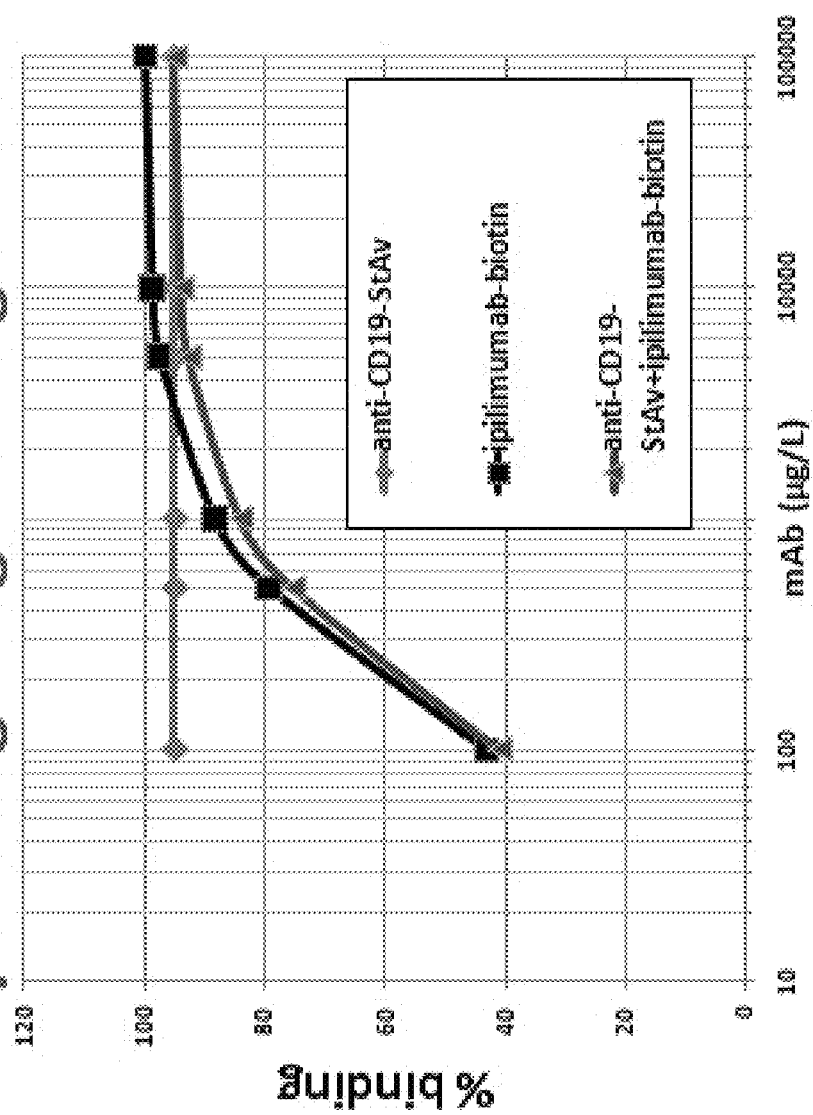
FIG. 4 is a graph illustrating the use of the law of mass action calculations to establish the binding curve of pretargeting anti-CTLA-4 sensitized T-cells. Step 1: saturation of CD19 antigens on B cells with a streptavidin labeled anti-CD19 mAb (♦); step 2: following the clearance of unbounded anti-CD19 mAb, a biotin-labeled anti-CTLA-4 mAb is administered to saturate CTLA-4 on T-cells (■); step 3: formation of complexes between anti-CD19 mAb-StAv-labeled B cells and CTLA-4-biotin-labeled T-cells (▲). Above 1 mg/L concentration (~5 mg/patient ~70 kgbw) of the anti-CTLA-4-biotin mAb more than 80% of anti-CD19-StAv carrying B cells will bind CTLA-4-biotin labeled T-cells.

The efficiency of pretargeting T-cells with a biotin-labeled anti-CTLA-4 for the B-cell antigen CD19 is calculated, using $K_D$ values and the law of mass action. This calculation demonstrates that significantly smaller concentration of biotin-labeled anti-CTLA-4 antibody is sufficient to mobilize T-cells in contrast to using anti-CTLA-4 antibody alone as demonstrated in FIG. 4. Assuming that 10% of T-cells were CTLA-4 positive, more than 80% of anti-CD19-StAv sensitized B cells will have been bound to anti-CTLA-4-biotin-sensitized T-cells, following the administration of anti-CTLA-4 antibody at a concentration>1 mg/L (i.e., about 5 mg per patient).

The calculations also reveal a noteworthy point of practical clinical value that the saturation curve essentially does not shift, if the ratio of the CTLA-4 positive to negative T-cells is increased from 10% to 100%. The great advantage of the present invention compared to prior art approaches is that the ~5 mg per patient anti-CTLA-4 antibody concentration is substantially lower than the lowest anti-CTLA-4 antibody dose group of 0.3 mg/kg (~18 mg per patient), which did cause mild autoimmunity in clinical trials when anti-CTLA-4 antibody was delivered as a single substance without pretargeting.

In the face of a pan-lymphocytic activation the task is to harness the immense forces liberated by the anti-CTLA-4 antibody blockade rather than trying to extinguish it by immune-suppressive treatments (Curran et al., Immunobiology, (2012)). Since mild-to-moderate immune-related events appeared even in the lowest 0.3 mg/kg anti-CTLA-4 antibody dose group, it is hoped that the co-stimulatory effect can be exploited by the use of the present invention at lower (perhaps much lower) concentrations than those used in the second phase III trial (Robert et al., N Engl J Med, 364, 2517-2526 (2011)).

An important advantage of anti-CTLA-4 antibody over the TGN1412 (anti-CD28 mAb) is that acute onset of a cytokine storm has not been described for any of the more than 6000 patients treated with anti-CTLA-4 antibody (Curran et al., Immunobiology, (2012)). However, prior art did not solve the problem to harness and regulate the enormous power released by the CTLA-4 blockade for the benefit of patients that the present invention provides.

The following examples further illustrate the invention but, of course, should not be construed as in any way limiting its scope.

To explore the clinical potential of pretargeting, two types of animal models can be used: either human tumors are transplanted into immunodeficient mice, followed by treatment of the tumor xenograft with targeted human lymphocytes, e.g. (Renner et al., Science, 264, 833-835 (1994)) or endogenous T-cells are targeted against murine tumors in syngeneic hosts. While syngeneic systems using immunocompetent mice provide a more realistic model for in vivo T-cell targeting as described in Example 1 of the present invention, human T-cells can only be tested on tumor xenograft in immunodeficient mice.

Leukemia generally provides better access than solid tumors to target antigens. Adult T-cell leukemia (ATL) develops in a small proportion of individuals infected with human T-cell lymphotrophic virus-I (HTLV-I). The leukemia consists of an overabundance of malignant activated T-cells, which are characterized by the expression of CD25 (interleukin 2 receptor a [IL-2Rα]) on their cell surfaces. The observation that IL-2Rα is not expressed by normal resting cells, but is expressed by ATL cells, provides the rationale for the use of monoclonal antibodies directed toward IL-2Rα to deliver therapeutic agents as described in Example 2 of the present invention.

Example 1

This example demonstrates the methodology for pretargeting anti-CTLA-4 immunotherapy for murine syngeneic adenocarcinoma.

The tumor cells are derived from mammary tumors induced spontaneously in mice by the mouse mammary tumor virus (MMTV). These cells express the gp52 envelope glycoprotein of MMTV on their surface, which is used as a tumor specific antigen. BALB/cAnN (BALB/c) mice are used between 8 and 14 weeks of age. The BALB/c MTV+ tumor line (64PT) is used for the generation of lung metastases. The P2AE12 (anti-gp52), an IgG2b mouse mAb against MTV gp52 conjugated to streptavidin (P2AE12-StrAv) is used for pretargeting the tumors.

A murine syngeneic adenocarcinoma lung metastases model is used. Examples of such techniques are provided in, e.g., (Bakacs et al., Int. Immunol., 7, 947-955 (1995)). Normal adult female BALB/c mice are injected intravenously in the tail vein with 0.2 ml PBS containing $5 \times 10^5$ 64PT-cells. This dose of cells gave rapidly growing tumors in all recipients whereas lower doses produced uneven growth of a few solitary tumors.

Treatment is either started 2 h after tumor was given, or treatment is delayed by 1, 2 and 4 days. Mice are first treated with intraperitoneal injections of P2AE12-StrAv (3, 10 and 30 μg each in 0.1 ml PBS). Control mice are given non-conjugated P2AE12 antibody.

Then, after 24 hours, which allows for antibody distribution and tumor localization, the unbound P2AE12-StrAv is cleared from the circulation by in vivo complexation with 100 μg (11.56 nmol) synthetic biotinylated poly(GalNAc)-clearing agent (sCA), which is injected intravenously to clear circulating P2AE12-StrAv conjugate from the blood in order to prevent it from binding the biotinylated anti-CTLA-4 antibody used in the following step as it is also demonstrated on FIG. 5.

Four hours after injection of the clearing agent the previously treated mice carrying lung metastases of adenocarcinoma are injected intraperitonealy with the biotin-anti-CTLA-4 antibody (3, 10 and 30 μg each in 0.1 ml PBS). This way, biotin-anti-CTLA-4 antibody is first bound to CTLA-4 positive T-cells and then the sensitized T-cells are rapidly and selectively accumulated to adenocarcinoma cells in the lungs. Non-biotinylated anti-CTLA-4 antibody is used for controls.

Tumor growth is assessed by following survival and by histological examination of H&E and Giemsa-stained lung cross sections. Survival curves are compared using the non-parametric Wilcoxon signed rank test. Extents of tumor infiltration are determined from Giemsa stained slides obtained at the largest cross-section of the lungs by either conventional pathological examination or by electronic scanning and analysis using an image analysis program (NIH Image, Version 1.55).

After about 14-28 days post-injection, administration of the second biotinylated anti-CTLA-4 antibody results in the reduction of numbers of tumors and reduction of tumor size compared to the control groups receiving administration of only anti-CTLA-4 antibody.

While this invention has been described with an emphasis upon preferred embodiments, it will be obvious to those of ordinary skill in the art that variations of the preferred embodiments may be used and that it is intended that the invention may be practiced otherwise than as specifically described herein. For example, the inventors expect skilled artisans to employ such variations as appropriate to target specific tumors. Using the appropriate animal models it is within the skill of artisans to employ other streptavidin conjugated Abs for pretargeting tumor-associated antigens (TAA) for carcinoembryonic antigen (CEA) for the treatment of colorectal cancer, tyrosinase (Tyr) for the treatment of melanoma or prostate-specific membrane antigen (PSMA) for the treatment of prostate cancer or for other types of tumors. Accordingly, this invention includes all modifications encompassed within the spirit and scope of the invention.

Example 2

This example demonstrates the methodology for pretargeted anti-CTLA-4 immunotherapy for adult T-cell leukemia.

1.5 to $2.0 \times 10^7$ human adult leukemia T-cells are injected intraperitonealy into non-obese diabetic/severe combined immunodeficient (SCID/NOD) mice as described by (Phillips et al., Cancer Res., 60, 6977-6984 (2000)). The therapy experiment is performed on these mice when their sIL-2Rα levels are more than 1000 pg/mL in the serum, which occurs approximately 10 to 14 days after tumor inoculation. Mice are treated in two groups: (1) the serum sIL-2Rα ranges from 1000 to 10000 pg/mL in the small tumor-burden therapeutic group; and (2) serum sIL-2Rα ranges from 20000 to 70000 pg/mL in the large tumor-burden therapeutic group.

A humanized anti-Tac (HAT) anti-IL-2Rα monoclonal antibody is conjugated to streptavidin (HAT-StrAv). Tumor-bearing mice are injected intravenously with 140 or 400 μg (0.67 or 1.91 nmol) of the streptavidin conjugated antibody specific to IL-2Rα for pretargeting.

After 24 hours, which allows for antibody distribution and tumor localization, the unbound HAT-StrAv is cleared from the circulation by in vivo complexation with 100 μg (11.56 nmol) synthetic biotinylated poly(GalNAc)-clearing agent (sCA), which is injected intravenously to clear circulating HAT-StrAv conjugate from the blood in order to prevent it from binding the biotinylated anti-CTLA-4 antibody used in the following step as described in FIG. 5.

T-cells may be combined ex vivo with the blocking agent, in this case the biotin-anti-CTLA-4 antibody. Peripheral human T-cells are isolated from cancer patients and are stimulated ex vivo, allowing them to differentiate into non-specific immune effector cells. For ex vivo stimulation, the host T-cells are aseptically removed, and are suspended in any suitable media, as known in the art. The cells are stimulated by any of a variety of protocols, preferably combinations of B7, anti-CD28 in combination with the blocking agents.

$4 \times 10^6$ cells, in 2 ml of culture medium containing the biotin-anti-CTLA-4 mAbs (generally, a daily dosage of active ingredient can be about 0.1 to 100 mg/kg of body weight), are incubated in a well of 24-well plates at 37° C., in a 5% $CO_2$ atmosphere for 2 days. The culture medium comprises RPMI 1640 medium supplemented with 10% heat inactivated fetal calf serum, 0.1 mM nonessential amino acids, 1 μM sodium pyruvate, 2 mM freshly prepared L-glutamine, 100 μg/ml streptomycin, 100 U/ml penicilin, 50 mg/ml gentamicin, 0.5 μg/ml fungizone (all from GIBCO, Grand Island, N.Y.) and $5 \times 10^{-5}$ M 2-ME (Sigma). The cells are harvested and washed. The initially stimulated cells are further cultured at $3 \times 10^5$/well in 2 ml of culture media with recombinant human IL-2 (available from Chiron Corp., Emeryville, Calif.; specific activity of 6 to $8 \times 10^6$ U/mg protein; units equivalent to 2-3 International U). After 3 days incubation in IL-2, the cells are collected, washed, counted to determine the degree of proliferation, and resuspended in media suitable for intravenous administration (e.g. physiological buffered saline solutions).

Four hours after injection of the clearing agent the previously treated, SCID/NOD mice carrying leukemia T-cells and already treated with HAT-StrAv are injected intravenously with the biotin-anti-CTLA-4 antibody treated peripheral human T-cells. This way, anti-CTLA-4 antibody bound T-cells are rapidly and selectively accumulated to leukemia cells. T-cells without the anti-CTLA-4 antibody incubation step are used as controls.

Measurements of the serum concentrations of the sIL-2Rα and/or soluble β-2-microglobulin (β2μ) are performed by using enzyme-linked immunosorbent assay at 2-week intervals after therapy to monitor growth of leukemia.

Body weight and complete blood count is measured before and after treatment (initially at weekly and subsequently at monthly intervals). The serum levels of creatinine, blood urea nitrogen (BUN), alanine aminotransferase, aspartate aminotransferase, creatine kinase, and γ-glutamyl transpeptidase is also measured at 2 and 5 weeks and at 2 and 4 months after treatment. Two to three animals in each group are killed at 5 weeks and at 2 and 4 months after treatment and the tissues (liver, kidneys, lung, spleen, intestine, and femur) is evaluated histopathologically. The serum levels of sIL-2Rα, β2M, and BUN, as well as body weight, at different time points for the different treatment groups is analyzed statistically using the t test for unpaired data. In terms of the mouse survival plots, StatView is used to generate Kaplan-Meier cumulative survival plots.

After about 14-28 days post-injection, administration of the T-cell/anti-CTLA-4 antibody complex results in significant survival advantage compared to control groups receiving only T-cells without the anti-CTLA-4 antibody.

Example 3

This example demonstrates the methodology for pretargeted anti-CTLA-4 immunotherapy for therapy of non-Hodgkin's lymphoma.

Approximately 7-9 weeks of age, female athymic BALB/c mice (NCI/Charles River Laboratories, Frederick, Md., USA) are implanted s.c. with $1 \times 10^7$ Ramos human B-cell lymphoma cells/0.2 ml in the hind flank. When tumors are ~1.0 cm diameter, treatment is initiated. The humanized streptavidin conjugated anti-CD20 $IgG_1$, IMMU-106 antibody (CD20-StrAv) is injected first for pretargeting as described in (Stein et al., Clin Cancer Res., 10, 2868-2878 (2004)).

Tumor-bearing mice are injected intravenously with 140 or 400 μg (0.67 or 1.91 nmol) of the humanized streptavidin conjugated anti-CD20 $IgG_1$, IMMU-106 antibody (CD20-StrAv). After 24 hours, which allows for antibody distribution and tumor localization, the unbound CD20-StrAv is cleared from the circulation by in vivo complexation with 100 μg (11.56 nmol) synthetic biotinylated poly(GalNAc)-clearing agent (sCA), which is injected intravenously to clear circulating CD20-StrAv conjugate from the blood in order to prevent it from binding the biotinylated anti-CTLA-4 antibody used in the following step described in FIG. 5.

T-cells are combined ex vivo with the blocking agent, the biotin-anti-CTLA-4 antibody. Peripheral human T-cells are isolated from cancer patients and are stimulated ex vivo, allowing them to differentiate into non-specific immune effector cells. For ex vivo stimulation, the host T-cells are aseptically removed, and are suspended in any suitable media, as known in the art. The cells are stimulated by any of a variety of protocols, particularly combinations of B7 and anti-CD28 in combination with the blocking agents.

$4 \times 10^6$ cells, in 2 ml of culture medium containing the biotin-anti-CTLA-4 mAbs (generally, a daily dosage of active ingredient can be about 0.1 to 100 mg/kg of body weight), are incubated in a well of 24-well plates at 37° C., in a 5% $CO_2$ atmosphere for 2 days. The culture medium comprises RPMI 1640 medium supplemented with 10% heat inactivated fetal calf serum, 0.1 mM nonessential amino acids, 1 μM sodium pyruvate, 2 mM freshly prepared L-glutamine, 100 μg/ml streptomycin, 100 U/ml penicillin, 50 mg/ml gentamicin, 0.5 μg/ml fungizone (all from GIBCO, Grand Island, N.Y.) and $5 \times 10^{-5}$ M 2-ME (Sigma). The cells are harvested and washed.

The initially stimulated cells are further cultured at $3 \times 10^5$/well in 2 ml of culture media with recombinant human IL-2 (available from Chiron Corp., Emeryville, Calif.; specific activity of 6 to $8 \times 10^6$ U/mg protein; units equivalent to 2-3 International U). After 3 days incubation in IL-2, the cells are collected, washed, counted to determine the degree of proliferation, and resuspended in media suitable for intravenous administration (e.g. physiological buffered saline solutions).

Four hours after injection of the clearing agent the previously treated, athymic BALB/c mice carrying the human B cell lymphoma and already treated with CD20-StrAv are injected intravenously with the biotin-anti-CTLA-4 antibody treated peripheral human T-cells. This way, anti-CTLA-4 antibody bound T-cells are rapidly and selectively accumulated to lymphoma cells. T-cells without the anti-CTLA-4 antibody incubation step are used as controls.

Body weights and tumor measurements (three dimensions measured by caliper) are made on the day of treatment and then 1-2 times per week until tumor sizes exceeded 2.5 $cm^3$. Survival is defined as the time for the tumor to reach 2.5 $cm^3$. If body weights decreases by more than 20% without evidence of excessive tumor growth, the mice are euthanized and censored for death due to toxicity. Statistical comparisons of survival is based on the log-rank test of Kaplan-Meier survival curves, as provided by Prism 4.0 software (GraphPad Software Inc., San Diego, Calif., USA). Comparisons of % ID/g or tumor/non-tumor (T/NT) ratios are determined by a Student's t-test. Body weight and complete blood count is measured before and after treatment (initially at weekly and subsequently at monthly intervals). The serum levels of creatinine, blood urea nitrogen (BUN), alanine aminotransferase, aspartate aminotransferase, creatine kinase, and γ-glutamyl transpeptidase is also measured at 2 and 5 weeks and at 2 and 4 months after treatment. Two to three animals in each group are killed at 5 weeks and at 2 and 4 months after treatment and the tissues (liver, kidneys, lung, spleen, intestine, and femur) is evaluated histopathologically.

After about 14-28 days post-injection, administration of the T-cell and biotinylated anti-CTLA-4 antibody results in the reduction of numbers of tumors and reduction of tumor size compared to control groups receiving administration of only anti-CTLA-4 antibody.

Example 4

This example demonstrates the methodology for pretargeting anti-CTLA-4 immunotherapy for murine colorectal carcinoma metastases.

This is a modified version of the pretargeted radioimmunotherapy of colorectal cancer metastases described in (Frampas et al., Eur. J. Nucl. Med. Mol. Imaging, 38, 2153-2164 (2011)). Compared to conventional direct anti-CTLA-4 therapy, the pre-targeting approach provides separate administrations of the tumor targeting and T-cell stimulating antibodies, respectively. The treatment protocol is optimized for the main parameters that influence pre-targeting efficiency: molar doses, structure of each compound and the time interval between injections. The pre-targeting time interval is of major importance. A too-short interval may lead to insufficient elimination of circulating tumor specific streptavidin conjugated antibody and to the formation of complexes on biotin-anti-CTLA-4 antibody sensitized T-cells that reduce efficacy of the therapy. If too long, the streptavidin conjugated antibody may clear from the tumor target before the biotin-anti-CTLA-4 antibody sensitized T-cells are available.

The LS-174T human colonic carcinoma cell line is used (obtained from the American Type Culture Collection), which strongly expresses CEA. Aggregated cells are prepared by mechanical means without trypsinization and suspended in saline solution. NMRI-nu (nu/nu) female mice (10-12 weeks old, weight 20-25 g) housed under standard conditions are anesthetized by intraperitoneal injection of 0.2 ml of anesthetic mixture. For subcutaneous tumors, $1\times10^6$ isolated cells in 0.2 ml of sterile physiologic serum are injected into the right flank. For hepatic tumors, a short median incision is made and LS-174T Luc+aggregated cells ($1\times10^6$ suspended in 0.1 ml sterile physiologic serum) are injected into the portal vein via a 30-G needle. Antibodies are injected via the tail vein. The humanized monoclonal antibody hMN-14 (labetuzumab), which has binding specificity for human CEACAM5, is conjugated to streptavidin and used for pre-targeting.

Treatment is either started 2 h after tumor was given, or treatment is delayed by 1, 2 and 4 days. Mice are first treated with intraperitoneal injections of hMN-14-StrAv (3, 10 and 30 μg each in 0.1 ml PBS). Control mice are given non-conjugated hMN-14 antibody.

After 24 h, which allows for antibody distribution and tumor localization, the unbound hMN-14-StrAv is cleared from the circulation by in vivo complexation with 100 μg (11.56 nmol) synthetic biotinylated poly(GalNAc)-clearing agent (sCA), which is injected intravenously to clear circulating hMN-14-StrAv conjugate from the blood in order to prevent it from binding the biotinylated anti-CTLA-4 antibody used in the following step as shown in FIG. 5.

Four hours after injection of the clearing agent the previously treated mice carrying liver metastases of colorectal carcinoma are injected intraperitonealy with the biotin-anti-CTLA-4 antibody (3, 10 and 30 μg each in 0.1 ml PBS). This way, biotin-anti-CTLA-4 antibody is bound first to CTLA-4 positive T-cells and then the sensitized T-cells are rapidly and selectively accumulate to colorectal carcinoma cells in the liver. Non-biotinylated anti-CTLA-4 antibody is used for controls.

Tumor growth is assessed by following survival and by histological examination of H&E and Giemsa-stained liver cross sections. Survival curves are compared using the non-parametric Wilcoxon signed rank test. Extents of tumor infiltration are determined from Giemsa stained slides obtained at the largest cross-section of the liver by either conventional pathological examination or by electronic scanning and analysis using an image analysis program (NIH Image, Version 1.55).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCE LIST

1. Bakacs, T. et al., A bispecific antibody prolongs survival in mice bearing lung metastases of syngeneic mammary adenocarcinoma. Int. Immunol., 7(6): 947-955 (1995).
2. Bakacs, T. et al., Interesting possibilities to improve the safety and efficacy of ipilimumab (Yervoy). Pharmacol. Res., 66(2): 192-197 (2012).
3. Beckman, R. A., Weiner, L. M., and Davis, H. M., Antibody constructs in cancer therapy: protein engineering strategies to improve exposure in solid tumors. Cancer, 109(2): 170-179 (2007).
4. Curran, M. A. et al., Response to "Ipilimumab (Yervoy) and the TGN1412 catastrophe". Immunobiology, 217 (2012) 590-592.
5. Farzaneh, L., Kasahara, N., and Farzaneh, F., The strange case of TGN1412. Cancer Immunol Immunother., 56(2): 129-134 (2007).
6. Frampas, E. et al., Pretargeted radioimmunotherapy of colorectal cancer metastases: models and pharmacokinetics predict influence of the physical and radiochemical properties of the radionuclide. Eur. J. Nucl. Med. Mol. Imaging, 38(12): 2153-2164 (2011).
7. Phillips, K. E. et al., IL-2Ralpha-Directed monoclonal antibodies provide effective therapy in a murine model of adult T-cell leukemia by a mechanism other than blockade of IL-2/IL-2Ralpha interaction. Cancer Res., 60(24): 6977-6984 (2000).
8. Porter, D. L. et al., Chimeric Antigen Receptor-Modified T Cells in Chronic Lymphoid Leukemia. N. Engl. J. Med., (2011) 365:725-733.
9. Renner, C. et al., Cure of xenografted human tumors by bispecific monoclonal antibodies and human T cells. Science, 264(5160): 833-835 (1994).
10. Robert, C. et al., Ipilimumab plus dacarbazine for previously untreated metastatic melanoma. N Engl J Med, 364(26): 2517-2526 (2011).
11. Rosenberg, S. A. et al., Adoptive cell transfer: a clinical path to effective cancer immunotherapy. Nat. Rev. Cancer, 8(4): 299-308 (2008).
12. Scott, A. M., Wolchok, J. D., and Old, L. J., Antibody therapy of cancer. Nat Rev Cancer, 12(4): 278-287 (2012).
13. Sharkey, R. M. and Goldenberg, D. M., Cancer radioimmunotherapy. Immunotherapy., 3(3): 349-370 (2011).
14. Stein, R. et al., Characterization of a new humanized anti-CD20 monoclonal antibody, IMMU-106, and Its use in combination with the humanized anti-CD22 antibody, epratuzumab, for the therapy of non-Hodgkin's lymphoma. Clin Cancer Res., 10(8): 2868-2878 (2004).
15. Szabados, T. and Bakacs, T., Sufficient to recognize self to attack non-self: Blueprint for a one-signal T cell model. Journal of Biological Systems, 19(2): 299-317 (2011).

What is claimed is:
1. A method of targeting human T-cells to human tumor cells in a human host, said method comprising:
(a) administering to said host a first tumor specific antibody binding to human carcinoembryonic antigen (CEA), CD19 or CD20, wherein said first tumor specific antibody is conjugated to a first member of a pair of specific binding moieties, in an amount sufficient to bind to the tumor cells in said host;

(b) administering to said host a clearing compound conjugated to the second member of said pair of specific binding moieties and allowing sufficient amount of time for the non-tumor bound fraction of said conjugated first antibody to be eliminated from said host;

(c) administering to said host a second T-cell specific antibody binding to human CTLA-4, wherein said second T-cell antibody is conjugated to the second member of said pair of specific binding moieties, in an amount sufficient to bind to the T-cells of said host and not more than about 5 mg; and (d) allowing sufficient amount of time for said first and second members of said pair of specific binding moieties to bind to each other, thereby targeting said T-cells to said tumor cells, wherein said method reduces immune related adverse events (irAEs) in a patient being treated for cancer relative to administration of anti-CTLA-4 antibody alone without said targeting.

2. The method of claim 1, wherein said first and second members of said pair of specific binding moieties are selected from the group consisting of avidin, streptavidin, and biotin.

3. The method of claim 2, wherein the first antibody is specific to carcinoembryonic antigen (CEA).

4. The method of claim 2, wherein the first antibody is specific to B cell surface antigen CD19 or CD20.

5. The method of claim 1 wherein the tumor cells expressed a tumor-associated antigen selected from the group consisting of CEA, CD19 and CD20, and the first tumor specific antibody is specific to said tumor-associated antigen.

6. A method of treating a tumor or cancer in a host comprising targeting T-cells to tumor or cancer cells by the method of claim 1, wherein cells of the tumor or cancer have a tumor-associated antigen selected from the group consisting of CEA, CD19 and CD20.

7. The method of claim 1, wherein
the first tumor specific antibody binds to CD20,
the first member of the pair of specific binding moieties is streptavidin,
the clearing compound is poly(GalNAc),
the second T-cell specific antibody binds to CTLA-4,
the second member of the pair of specific binding moieties is biotin.

8. A method of reducing irAEs in a patient being treated for cancer by administration of anti-CTLA-4 antibody, said method comprising first targeting T-cells to tumor or cancer cells by the method of claim 1, and subsequently administering a dose of not more than about 5 mg of the anti-CTLA-4 antibody to the patient.

9. The method of claim 6, wherein the tumor-associated antigen (TAA) is carcinoembryonic antigen (CEA).

10. The method of claim 1, wherein the second T-cell specific antibody binding to human CTLA-4 is ipilimumab.

11. The method of claim 1, wherein the first antibody is specific to B cell surface antigen CD19 or CD20.

12. The method of claim 1, wherein the clearing compound is poly(GalNAc).

13. The method of claim 1, wherein the second T-cell specific antibody binding to human CTLA-4 conjugated to the second member of said pair of specific binding moieties is combined ex vivo with T-cells prior to being administered to said host in step (c).

* * * * *